(12) United States Patent
Cottrell

(10) Patent No.: US 9,018,428 B2
(45) Date of Patent: *Apr. 28, 2015

(54) REACTOR AND AGITATOR USEFUL IN A PROCESS FOR MAKING 1-CHLORO-3,3,3-TRIFLUOROPROPENE

(71) Applicant: Honeywell International Inc., Morristown, NJ (US)

(72) Inventor: Stephen A. Cottrell, Churchville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/826,023

(22) Filed: Mar. 14, 2013

(65) Prior Publication Data

US 2014/0066670 A1    Mar. 6, 2014

Related U.S. Application Data

(60) Provisional application No. 61/697,373, filed on Sep. 6, 2012.

(51) Int. Cl.
*C07C 17/25* (2006.01)
*C07C 17/20* (2006.01)
(Continued)

(52) U.S. Cl.
CPC ............ *C07C 17/25* (2013.01); *B01J 19/0066* (2013.01); *C07C 17/093* (2013.01); *C07C 17/38* (2013.01); *C07C 17/383* (2013.01); *B01J 19/006* (2013.01); *B01J 19/0073* (2013.01); *B01J 19/02* (2013.01); *B01J 19/18* (2013.01); *B01J 19/26* (2013.01);

(Continued)

(58) Field of Classification Search
CPC ........................................................ C07C 17/25
USPC ......... 570/156, 155, 153, 226, 167, 165, 166, 570/230
See application file for complete search history.

(56) References Cited

U.S. PATENT DOCUMENTS 2,585,644 A * 2/1952 Burford et al. ................. 570/123
2,608,593 A * 8/1952 Fowler et al. .................. 570/123
(Continued)

FOREIGN PATENT DOCUMENTS

EP      0892771 B1    6/2003
EP      2484943 A1    8/2012
(Continued)

OTHER PUBLICATIONS

PCT ISR & Written Opinion issued in PCT/US2013/057186 dated Nov. 11, 2013.

*Primary Examiner* — Clinton Brooks
*Assistant Examiner* — Medhanit Bahta
(74) *Attorney, Agent, or Firm* — Bruce O. Bradford

(57) ABSTRACT

Disclosed is a reactor and agitator useful in a high pressure process for making 1-chloro-3,3,3-trifluoropropene (1233zd) from the reaction of 1,1,1,3,3-pentachloropropane (240fa) and HF, wherein the agitator includes one or more of the following design improvements:
(a) double mechanical seals with an inert barrier fluid or a single seal;
(b) ceramics on the rotating faces of the seal;
(c) ceramics on the static faces of seal;
(d) wetted o-rings constructed of spring-energized Teflon and PTFE wedge or dynamic o-ring designs; and
(e) wetted metal surfaces of the agitator constructed of a corrosion resistant alloy.

8 Claims, 2 Drawing Sheets

(51) Int. Cl.
*C07C 17/383* (2006.01)
*C07C 17/38* (2006.01)
*C07C 17/093* (2006.01)
*B01J 19/02* (2006.01)
*B01J 19/18* (2006.01)
*B01J 19/00* (2006.01)
*B01J 19/26* (2006.01)
*B01J 3/08* (2006.01)
*B01F 7/00* (2006.01)

(52) U.S. Cl.
CPC .......... *B01J 3/08* (2013.01); *B01J 2219/00006* (2013.01); *B01J 2219/0004* (2013.01); *B01J 2219/00094* (2013.01); *B01J 2219/00123* (2013.01); *B01J 2219/00162* (2013.01); *B01J 2219/0218* (2013.01); *B01J 2219/0263* (2013.01); *B01J 2219/0277* (2013.01); *B01F 7/00033* (2013.01)

(56) References Cited

U.S. PATENT DOCUMENTS

| | | | |
|---|---|---|---|
| 3,877,706 A | | 4/1975 | Haas et al. |
| 4,202,553 A | * | 5/1980 | Kropp ............................. 277/366 |
| 6,362,383 B1 | | 3/2002 | Wilmet et al. |
| 6,844,475 B1 | * | 1/2005 | Tung et al. ..................... 570/168 |
| 2005/0019487 A1 | | 1/2005 | Braun et al. |
| 2007/0118003 A1 | * | 5/2007 | Bradley et al. ................ 570/167 |
| 2009/0287027 A1 | | 11/2009 | Merkel et al. |
| 2011/0105807 A1 | | 5/2011 | Kopkalli et al. |
| 2011/0218370 A1 | * | 9/2011 | Elsheikh et al. ............... 570/236 |
| 2012/0296127 A1 | | 11/2012 | Cottrell et al. |

FOREIGN PATENT DOCUMENTS

| | | |
|---|---|---|
| WO | 2010059496 A1 | 5/2010 |
| WO | 2010111067 A1 | 9/2010 |
| WO | WO 2010111067 A1 * | 9/2010 |
| WO | 2012030797 A2 | 3/2012 |

* cited by examiner

REACTOR AND AGITATOR USEFUL IN A PROCESS FOR MAKING 1-CHLORO-3,3,3-TRIFLUOROPROPENE

CROSS-REFERENCE TO RELATED APPLICATION

This application claims domestic priority under 35 U.S.C. 119(e) to commonly owned U.S. Provisional Application Ser. No. 61/697,373, filed 6 Sep. 2012, the disclosure of which is hereby incorporated herein by reference.

BACKGROUND OF THE INVENTION

This invention is directed to an improved design for a reactor and agitator useful in a process for making 1-chloro-3,3,3-trifluoropropene (1233zd) from the reaction of 1,1,1,3,3-pentachloropropane (240fa) and HF. The compound 1233zd is a low global warming compound that has applications as a replacement for high global warming materials, for example in foam blowing and aerosol propellant applications.

The designation 1233 is used herein to refer to all trifluoro, monochloro propenes, namely olefin compounds having the general formula $C_3H_2ClF_3$. The designation 1233zd is used herein generically to refer to 1,1,1-trifluo-3-chloro-propene, independent of whether it is the cis form or the trans form. The terms "cis-1233zd" and "trans-1233zd" are used herein to describe the cis- and trans-forms of 1,1,1-trifluo-3-chloro-propene, respectively. The designation "1233zd" therefore includes within its scope cis-1233zd, trans-1233zd, and all combinations and mixtures of these.

U.S. Pat. No. 6,844,475 teaches a process for producing 1233zd from 240fa at low pressure and at temperatures lower than 150° C. The disclosure of this patent is hereby incorporated herein by reference.

U.S. Pat. No. 6,362,383 teaches a process for preparing 1,1,1,3,3-pentafluoropropane (245fa) by (1) a first reaction step in which 1,1,1,3,3-pentachloropropane (240fa) is reacted with hydrogen fluoride in the liquid phase in the presence of a first hydrofluorination catalyst under conditions that are suitable for obtaining a mixture of reaction products comprising 1-chloro-3,3,3-trifluoropropene (1233zd) in substantial amount, and (2) a second reaction step in which the 1-chloro-3,3,3-trifluoropropene (1233zd) obtained from the first step is reacted with hydrogen fluoride in the liquid phase in the presence of a second hydrofluorination catalyst, and preferably while hydrogen chloride is continuously fed in, in order to obtain 1,1,1,3,3-pentafluoropropane (245fa). The disclosure of this patent is hereby incorporated herein by reference.

U.S. Patent Publication No. 2012-0296127 discloses a high pressure process to produce 1233zd, operating at moderate temperatures. The disclosure of this patent application is hereby incorporated herein by reference. In this process, hydrogen fluoride (HF) is used as a raw material and HCl is produced as a co-product. Agitation is required for the process. Because of the corrosive nature of the chemicals used and generated in the reaction, designing an agitator that will have an appropriate life is a challenge.

The present invention provides a suitable reactor and in particular an agitator used therein for conducting this process, wherein the agitator is constructed with materials that resist the effects of the corrosive chemicals of the reaction.

SUMMARY OF THE INVENTION

This invention is directed to improved designs for a liquid phase reactor and agitator useful in a high pressure process for making 1-chloro-3,3,3-trifluoropropene (1233zd) from the reaction of 1,1,1,3,3-pentachloropropane (240fa) and HF, in which HCl is produced as a co-product. Given that agitation is required for this process both the reactor vessel and the agitator must be made out of corrosion resistant materials in order to have a useful lifetime for conducting this process.

Thus, one embodiment of the invention is directed to a reactor and agitator useful in a high pressure process for making 1-chloro-3,3,3-trifluoropropene (1233zd) from the reaction of 1,1,1,3,3-pentachloropropane (240fa) and HF, wherein the agitator includes one or more of the following improvements:

(a) double mechanical seals with an inert barrier fluid or a single seal;
(b) ceramics (parts or coatings) are employed on the rotating faces of the seal;
(c) ceramics (parts or coatings) may also be used on the static faces of seal;
(d) wetted o-rings constructed of spring-energized Teflon and PTFE wedge or dynamic o-ring designs; and
(e) wetted metal surfaces of the agitator constructed of an appropriate corrosion resistant alloy.

The high pressure liquid phase reaction of 240 and HF, with or without a catalyst, yields a product stream comprising 1233zd, byproducts, HCl and unreacted HF. In certain embodiments the pressure range is from 150 psig to 600 psig. In certain embodiments, a more preferred pressure range is from 230 psig to 500 psig and a most preferred pressure range is from 350 psig to 450 psig.

In certain embodiments, the catalyst choices are selected from known Lewis acid catalysts. The preferred catalysts are $TiCl_4$ or $SbCl_5$, with $TiCl_4$ being more preferred. In certain embodiments, the most preferred choice is operation of the reactor without employing any catalyst.

The typical byproducts observed in the reaction stream are precursors to 1233zd such as 241fa, 242fa, and 243fa. These can easily be separated from the reaction stream using known techniques and recycled.

In one embodiment of the high pressure process for making 1233zd, the reactants 240fa and HF are fed to a continuously stirred or agitated reactor, having the improved agitator design described herein, operating at high pressure, and;

(a) the resulting product stream comprising 1233zd, HCl, HF, and other byproducts are distilled and the bottoms product, rich in HF, is recycled to the reactor;
(b) the overhead product from the distillation column is fed to a second distillation column to remove the HCl;
(c) the HCl in the overhead stream is scrubbed with water and recovered as an aqueous solution;
(d) the bottom stream from the second distillation column is then phase separated to recover HF;
(e) the HF rich top layer of the phase separation is recycled back to the reactor; and
(f) the phase separation bottom layer components including the desired 1233zd are scrubbed, dried and distilled to meet commercial product specifications.

As described above, in a high pressure process for the production of 1233zd, the operating conditions of the reactor are extremely aggressive and the process employs reactant materials that are highly corrosive under these reaction conditions. It has been found that certain design characteristics are especially preferred for the agitator design herein, including:

(a) double mechanical seal with an inert barrier fluid such as fluorolube or a single seal.
(b) silicon carbide (parts or coatings) on the rotating faces of the seal.

(c) silicon carbide (parts or coatings) may also be used on the static faces of seal.
(d) wetted o-rings constructed of spring-energized Teflon (such as the OMNISEAL brand made by St. Gobain) and PTFE wedge or dynamic o-ring design
(e) wetted metal surfaces of the agitator constructed of an appropriate nickel alloy such as Alloy 20, the Hastelloy alloys or the Inconel alloys.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, in the high pressure process for the production of 1233zd, the operating conditions of the reactor are extremely aggressive (e.g., 140° C. and 400 psig) and the process employs reactant materials that are highly corrosive under these reaction conditions. The process requires agitation to allow the reaction to proceed. As such, the design of the agitator is critical to ensure an appropriate operating lifetime in the harsh conditions. The present invention is directed to one such reactor and agitator design.

Key Characteristics of Agitator Design:
(a) Double mechanical seal with an inert barrier fluid such as fluorolube.
(b) Silicon Carbide ceramics (or the like) on the rotating faces of the seal.
(c) Silicon Carbide ceramics (or the like) may also be used on the static faces of seal.
(d) Perfluoroelastomer o-rings and PTFE wedge design
(e) Wetted metal surfaces of the agitator are constructed of an appropriate nickel alloy such as Alloy 20, the Hastelloy alloys or the Inconel alloys.

Figure 1:
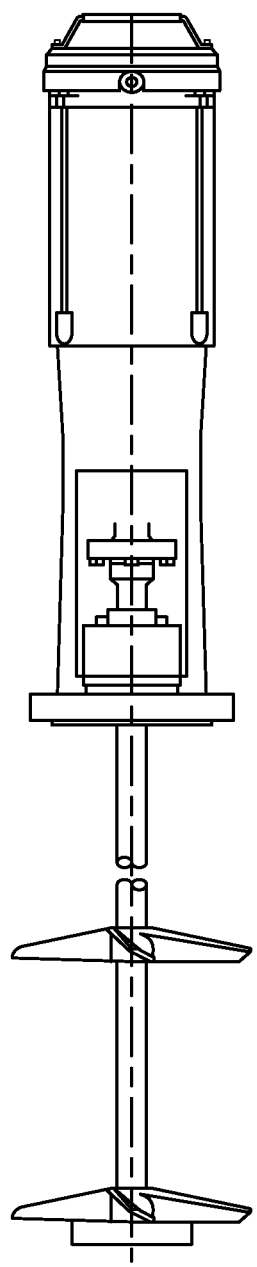
FIG. 1 illustrates a preferred agitator design of the present invention.

As shown in FIG. 1, an agitator according to the present invention includes a double mechanical seal consisting of a ceramic material, e.g., silicon carbide and equivalents, on the rotating faces, wetted parts that are constructed of an appropriate nickel alloy, and spring-energized o-rings. The agitator may be installed in a top or bottom mount position.

Figure 2:
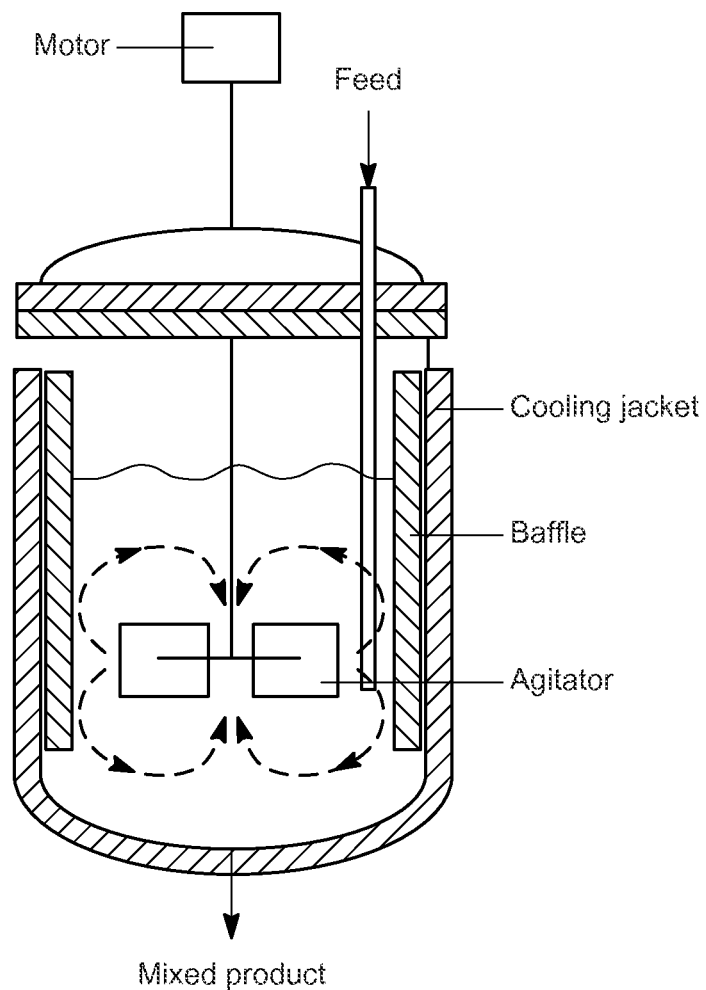
FIG. 2 illustrates a preferred continuous stirred tank reactor vessel design of the present invention.

As shown in FIG. 2, a reactor vessel according to the present invention includes an agitator of the style of FIG. 1, materials of construction of an appropriate nickel, alloy (either solid or clad), and may contain an external or internal heating or cooling system. The design may be modified to feed reactants in the liquid or vapor phase and may be fed to the bottom or top of the vessel.

Corrosion resistant alloys are known and are preferred materials used in the construction of the reactor vessel and agitator of the present invention. Some of the commercially available corrosion resistant alloys include the following:
(a) Nickel 200

Nickel 200 is commercially pure (99.6%) wrought nickel. It has good mechanical properties and excellent resistance to many corrosive environments.
(b) Monel® 400

Monel® nickel-copper alloy 400 is a solid solution alloy that may be hardened only by cold working. It has high strength and toughness over a wide temperature range and excellent resistance to many corrosive environments.
(c) Inconel® 600

Inconel® nickel-chromium-iron alloy 600 is a standard engineering material for applications which require resistance to corrosion and heat. The alloy shows resistance to oxidizing conditions at high temperatures or in corrosive solutions.
(d) Inconel® 625

Inconel® nickel chromium alloy 625 is used for its high strength, excellent fabricability (including joining), and outstanding corrosion resistance.
(e) INCO C-276

INCO alloy C-276 is known for its outstanding corrosion resistance in a wide range of severe media. The high nickel and molybdenum contents provide good corrosion resistance in reducing environments while chromium imparts resistance to oxidizing media.
(f) Incoloy® Alloy 800

Incoloy® alloy 800 is a widely used material of construction for equipment that must have high strength and resist oxidation, carburization, and other harmful effects of high-temperature exposure. The chromium in the alloy imparts resistance to oxidation and corrosion.
(g) Incoloy® 825

Incoloy® alloy 825 is a nickel-iron-chromium alloy with additions of molybdenum, copper and titanium. The alloy's chemical composition is designed to provide exceptional resistance to many corrosive environments.
(h) Alloy 020

INCO alloy 020 is an austenitic nickel-iron-chromium alloy with additions of copper and molybdenum. The nickel content makes INCO alloy 020 resistant to chloride-ion stress-corrosion cracking Copper and molybdenum give resistance to reducing environments. The molybdenum content also provides good resistance to pitting and crevice corrosion. The chromium gives resistance to oxidizing environments.
(i) Hastelloy®

Hastelloy® is the trademark name for a range of twenty two different highly corrosion-resistant metal alloys loosely grouped by the metallurgical industry under the material term "superalloys" or "high-performance alloys". The predominant alloying ingredient is typically the transition metal nickel.

Working Example

An agitator is constructed of Alloy 20 wetted parts and a double mechanical seal with fluorolube barrier fluid, silicon carbide on all seal faces, spring-energized Teflon o-rings and a PTFE wedge system was operated at conditions ranging from 100 to 400 psig and 90° to 145° C. in a process to produce HFCO-1233zd from HF and HCC-240. The agitator operated successfully for several months.

Comparative Example 1

An agitator constructed of Alloy 020 wetted parts and a double mechanical seal with fluorolube barrier fluid, silicon carbide on all seal faces, perfluoroelastomer o-rings and a PTFE wedge system was operated at conditions ranging from 100 to 400 psig and 90° to 145° C. in a process to produce HFCO-1233zd from HF and HCC-240. The agitator seal system failed after 3 weeks of operation due to chemical attack of the perfluoroestomer wetted o-rings.

Comparative Example 2

An agitator constructed of Alloy 020 wetted parts and a double mechanical seal with fluorolube barrier fluid, tungsten carbide on the rotating seal face, perfluoroelastomer o-rings and a PTFE wedge system was operated at conditions ranging from 100 to 150 psig and 90° to 100° C. in a process to produce HFCO-1233zd from HF and HCC-240. The agitator seal system failed after 2 weeks of operation due to failure of the seal faces.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the manufacture of 1233zd comprising the steps of:
    (a) reacting 240fa and HF without a catalyst in an agitator stirred reactor, wherein the agitator comprises wetted metal surfaces and two spaced-apart sets of agitator blades mounted on an agitator shaft, wherein the wetted metal surfaces of the agitator comprise a corrosion resistant alloy selected from the group consisting of Alloy 020, the Hastelloy alloys and the Inconel alloys, and the reactor is operated at a pressure range of 350 psig to 450 psig and at a temperature range of from 90° C. to 145° C. to produce a product stream comprising 1233zd, HCl, HF, and other byproducts;
    (b) distilling the product stream from step (a) into a first overhead product and a first bottoms product rich in HF;
    (c) distilling the first overhead product from step (b) to form a second overhead product containing HCl and a second bottoms product containing organic components and HF;
    (d) phase separating the second bottoms product from step (c) to separate the HF from the organic components; and
    (e) scrubbing, drying, and distilling the organic components from step (d) to provide purified 1233zd.

2. The process of claim 1, wherein the HF from step (b) is recycled to the reactor.

3. The process of claim 1, wherein the HCl from step (c) is scrubbed with water and optionally recovered as an aqueous solution.

4. The process of claim 1, wherein the HF from the phase separation in step (d) is recycled back to the reactor.

5. A process for the manufacture of 1233zd comprising the steps of:
    (a) reacting 240fa and HF with a catalyst in an agitator stirred reactor, wherein the agitator comprises wetted metal surfaces and two spaced-apart sets of agitator blades mounted on an agitator shaft, wherein the wetted metal surfaces of the agitator comprise a corrosion resistant alloy selected from the group consisting of Alloy 020, the Hastelloy alloys and the Inconel alloys, and the reactor is operated at a pressure range of 350 psig to 450 psig and at a temperature range of from 90° C. to 145° C. to produce a product stream comprising 1233zd, HCl, HF, and other byproducts;
    (b) distilling the product stream from step (a) into a first overhead product and a first bottoms product rich in HF;
    (c) distilling the first overhead product from step (b) to form a second overhead product containing HCl and a second bottoms product containing organic components and HF;
    (d) phase separating the second bottoms product from step (c) to separate the HF from the organic components; and
    (e) scrubbing, drying, and distilling the organic components from step (d) to provide purified 1233zd.

6. The process of claim 5, wherein the catalyst comprises one or more Lewis acid catalysts.

7. The process of claim 6, wherein the Lewis Acid catalyst is selected from the group consisting of $TiCl_4$, $SbCl_5$, and mixtures thereof.

8. The process of claim 7, wherein the catalyst is $TiCl_4$.

* * * * *